US006350305B1

(12) United States Patent
King et al.

(10) Patent No.: US 6,350,305 B1
(45) Date of Patent: Feb. 26, 2002

(54) SELECTED POLYMERIC FURANONE MAGENTA COLORANTS

(75) Inventors: Clifford R. King, Salem; Jeffery H. Banning, Hillsboro, both of OR (US)

(73) Assignee: Xerox Corporation, Stamford, CT (US)

( * ) Notice: Subject to any disclaimer, the term of this patent is extended or adjusted under 35 U.S.C. 154(b) by 0 days.

(21) Appl. No.: 09/416,208

(22) Filed: Oct. 8, 1999

Related U.S. Application Data

(62) Division of application No. 09/188,010, filed on Nov. 6, 1998, now abandoned.

(51) Int. Cl.[7] .......................... C09D 11/02; C09D 11/10; C07D 307/58; C07D 307/52
(52) U.S. Cl. ..................... 106/31.29; 8/647; 106/31.01; 106/31.13; 106/31.43; 106/31.45; 106/31.61; 106/31.75; 523/161; 528/49; 528/73; 528/291; 528/288; 528/341; 528/347; 528/349; 528/362; 560/24; 560/25; 560/26; 560/32; 560/33; 560/115; 560/157; 560/158; 549/321
(58) Field of Search .............................. 8/647; 549/321; 523/161; 106/31.01, 31.13, 31.29, 31.43, 31.45, 31.61, 31.75; 528/73, 49, 291, 288, 341, 347, 349, 362; 560/24, 25, 26, 32, 33, 115, 157, 158

(56) References Cited

U.S. PATENT DOCUMENTS

| | | | |
|---|---|---|---|
| 3,468,912 A | 9/1969 | Ford et al. | 549/321 |
| 3,507,648 A * | 4/1970 | Ford et al. | 430/83 |
| 3,661,899 A | 5/1972 | Ford et al. | 546/284.4 |
| 4,889,560 A | 12/1989 | Jaeger et al. | 106/27 |
| 4,889,761 A | 12/1989 | Titterington et al. | 428/195 |
| 5,231,135 A | 7/1993 | Machell et al. | 525/123 |
| 5,372,852 A | 12/1994 | Titterington et al. | 427/288 |
| 5,496,879 A | 3/1996 | Gribel et al. | 524/320 |
| 5,621,022 A | 4/1997 | Jaeger et al. | 523/161 |
| 5,700,851 A | 12/1997 | Banning et al. | 523/160 |
| 5,750,604 A | 5/1998 | Banning et al. | 524/187 |
| 5,780,528 A | 7/1998 | Titterington et al. | 523/161 |
| 5,782,966 A | 7/1998 | Bui et al. | 106/31.43 |
| 5,783,658 A | 7/1998 | Banning et al. | 528/590 |
| 5,827,918 A | 10/1998 | Titterington et al. | 524/590 |
| 5,830,942 A | 11/1998 | King et al. | 524/590 |

FOREIGN PATENT DOCUMENTS

| | | |
|---|---|---|
| DE | 4205636 | 2/1992 |
| DE | 4205713 | 2/1992 |

OTHER PUBLICATIONS

"The Chemistry And Application Of Dyes", 4 pages, 1990, Plenum Press.

"Organic Syntheses", Collective vol. II, John Wiley & Sons, 480–481, 1966.

* cited by examiner

*Primary Examiner*—Rabon Sergent
(74) *Attorney, Agent, or Firm*—Judith L. Byorick

(57) ABSTRACT

A polymeric furanone magenta colorant is disclosed that contains a furanone magenta chromophore having a furanone adduct, the adduct containing at least one alkoxylated phenyl radical, the chromophore further being derived from at least one aromatic aldehyde having a para-nitrogen and containing electron donating groups selected from the group consisting of alkyls, cycloalkyls, and oligomers or polymers derived from alkyleneoxy or aryleneoxy moieties. The colorant can be utilized in resins, waxes and inks.

16 Claims, No Drawings

SELECTED POLYMERIC FURANONE MAGENTA COLORANTS

This application is a divisional of U.S. patent application Ser. No. 09/188,010, filed Nov. 6, 1998, now abandoned.

BACKGROUND OF THE INVENTION

1. Field of the Invention

The present invention relates to selected polymeric furanone magenta colorants and a process for making these colorants. Furthermore, the present invention relates to phase change inks containing these colorants as well as selected resins and waxes that incorporate these colorants therein.

2. Description of the Relevant Art

Phase change inks in digital printing applications (also sometimes called solid inks or hot melt inks) have in the past decade gained significant consumer acceptance as an alternative to more traditional printing systems such as offset printing, flexography printing, gravure printing, letterpress printing and the like. Phase change inks are especially desirable for the peripheral printing devices associated with computer technology, as well as being suitable for use in other printing technologies such as gravure printing applications as referenced in U.S. Pat. No. 5,496,879 and German Patent Publications DE 4205636AL and DE4205713AL assigned to Siegwerk Farbenfabrik Keller, Dr. Rung & Co.

In general, phase change inks are in the solid phase at ambient temperature, but exist in the liquid phase at the elevated operating temperature of an ink jet printing device. At the jet operating temperature, droplets of liquid ink are ejected from the printing device and, when the ink droplets contact the surface of the printing media, they quickly solidify to form a predetermined pattern of solidified ink drops.

They are easy to use and safe. They can be easily loaded into the printer by the user, generally in the form of solid sticks of yellow, magenta, cyan and black ink having a solid consistency similar to children's crayons. Inside the printer, these inks are melted at an elevated temperature in a printhead having a number of orifices, through which the melted ink will be ejected onto the desired substrate such as media like paper or an overhead transparency film. Alternatively, the melted ink may be transferred to a rotating drum and then transferred to the substrate. As the ink cools on the substrate, it re-solidifies into the desired image. This resolidification process, or phase change, is instantaneous and a printed, dry image is thus made upon leaving the printer, which is available immediately to the user.

These phase change inks contain no solvents or diluent that can lead to undesired emissions. In all, the use and specific design of the phase change ink addresses many of the limitations of more traditional ink and printing processes.

Furthermore, because the ink is in cool, solid form at any time when the user can actually come in contact with the ink, and the ink is in a molten state only inside the printer (inaccessible to the user), it is generally safe to use. These inks also have long-term stability for shipping and long storage times.

The phase change inks generally comprise a phase change ink carrier composition, which is combined with at least one compatible phase change ink colorant. The carrier composition has been generally composed of resins, fatty acid amides and resin derived materials. Also, plasticizers, waxes, antioxidants and the like have been added to the carrier composition. Generally the resins used must be water-insoluble and the carrier composition may contain no ingredients that are volatile at the jetting temperatures employed. Also, these carrier ingredients should be chemically stable so as not to lose their chemical identity over time and/or under elevated temperature conditions.

Preferably, a colored phase change ink will be formed by combining the above described ink carrier composition with compatible colorant material, preferably subtractive primary colorants. The subtractive primary colored phase change inks comprise four component dyes, namely, cyan, magenta, yellow and black. U.S. Pat. Nos. 4,889,560 and 5,372,852 teach the preferred subtractive primary colorants employed. Typically these may comprise dyes from the classes of Color Index (C.I.) Solvent Dyes, C.I. Disperse Dyes, modified C.I. Acid and Direct Dyes, as well as a limited number of C.I. Basic Dyes. Also suitable as colorants are appropriate polymeric dyes, such as those described in U.S. Pat. No. 5,621,022 and available from Milliken & Company as Milliken Ink Yellow 869, Milliken Ink Blue 92, Milliken Ink Red 357, Milliken Ink Yellow 1800, Milliken Ink Black 8915-67, uncut Reactant Orange X-38, uncut Reactant Blue X-17, and uncut Reactant Violet X-80 or those described in U.S. Pat. No. 5,231,135.

Colored resin reaction products such as those described in U.S. Pat. No. 5,780,528 issued Jul. 14, 1998, and assigned to the assignee of the present invention, are also suitable colorants.

Polymeric colorants are increasingly being utilized in preparing commercial phase change ink jet inks, as well as potentially for use in other applications, such as gravure printing, and other types of inks and coating applications where coloration is desired. For example, the specific class of polymeric dyes characterized by: (1) an organic chromophore having (2) a polyoxyalkylene substituent and optionally (3) a carboxylic acid or non-reactive derivative thereof covalently bonded to the polyoxyalkylene substituent, as described in U.S. Pat. No. 5,621,022 (Jaeger et al.) possess several advantages; including:

(1) These polymeric dyes are very soluble in the phase change carrier composition and possess high water fastness and high resistance to "bleeding" or weeping of the color from the carrier composition when printed samples are subjected to high temperatures or humidity.

(2) These polymeric dyes are thermally stable in the carrier composition. This is important because the resulting phase change ink compositions may remain molten for weeks at a time in the ink jet printer, or otherwise at elevated temperatures.

(3) These polymeric dyes also act as a plasticizer for the formulation. This enables the formulator to replace at least a portion of the commercial plasticizer that is normally part of the formulations disclosed in the inks of U.S. Pat. Nos. 4,889,560 and 5,372,852.

(4) These polymeric dyes are compatible with each other and with most conventional powdered dyes currently used in phase change ink compositions. Thus, mixtures of inks of different colors do not form a precipitate when mixed together during the printing process. This compatibility also allows for the mixing of these polymeric dyes with powdered dyes of the same primary color into the same ink composition to achieve high color strengths that would not be possible with either dye type by itself.

While phase change ink compositions containing this class of polymeric dye colorants have had good commercial success, it must be noted that non-migrating, lightfast magenta colorants are absent from this class of polymeric dyes. The present invention provides a solution to the need for better non-migrating magenta colorants that possess the other advantages of this class of polymeric dyes.

BRIEF SUMMARY OF THE INVENTION

The present invention is based on the discovery of a new class of oligomeric or polymeric furanone magenta dyes. The dyes are useful in a number of applications, including phase change inks. This new class of furanone magenta dyes can be made by a new and commercially viable synthesis that avoids the use of particularly hazardous starting materials and intermediates.

Therefore, one aspect of the present invention is directed to an oligomeric or polymeric furanone magenta colorant comprising a 3-cyano-4-phenyl-2(5H)-furanone adduct wherein the phenyl radical possesses an oligo or polyoxyalkylene substituent. This 3-cyano-4-(p-polyoxyalkylenephenyl)-2(5H)-furanone moiety, referred to above as the furanone adduct, can be further condensed with a variety of electron rich benzaldehyde moieties to produce magenta colorants.

Another aspect of the present invention is directed to a process for making a polymeric furanone magenta colorant comprising the steps of:
(1) subjecting an alkoxylated acetophenone to a halogenation reaction to form a halogenated alkoxylated acetophenone;
(2) subjecting the halogenated alkoxylated acetophenone to an organocarboxylate substitution reaction to form the organocarboxylate ester of the alkoxylated acetophenone;
(3) condensing the organocarboxylate diester of the alkoxylated acetophenone with an alkylcyanoacetate in the presence of base to form an alkoxylated furanone adduct; and
(4) condensing the alkoxylated furanone adduct with an electron rich aromatic aldehyde to form a polymeric furanone magenta colorant having at least one alkoxylated phenyl radical and derived from at least one aromatic aldehyde having a para-nitrogen and containing electron donating groups selected from the group consisting of alkyls, cycloalkyls, and polymers derived from alkyleneoxy or aryleneoxy moieties.

Still another aspect of the present invention is directed to a phase change ink composition comprising the combination of a phase change ink carrier and an oligomeric or polymeric furanone magenta colorant that comprises a furanone magenta chromophore having at least one alkoxylated phenyl radical and derived from at least one aromatic aldehyde having a para-nitrogen and containing electron donating groups selected from the group consisting of alkyls, cycloalkyls, and polymers derived from alkyleneoxy or aryleneoxy moieties.

And still another aspect of the present invention is directed to an isocyanate-derived colored resin composition comprising the reaction product of:
(a) an isocyanate or diisocyanate; and
(b) at least one nucleophile comprising an oligomeric or polymeric furanone magenta colorant having at least one alkoxylated phenyl radical and derived from at least one aromatic aldehyde having a para-nitrogen and containing electron donating groups selected from the group consisting of alkyls, cycloalkyls, and polymers derived from alkyleneoxy or aryleneoxy moieties.

And a further aspect of the present invention is directed to an isocyanate-derived colored wax composition comprising the reaction product of:
(a) an isocyanate or a diisocyanate; and
(b) at least one nucleophile comprising an oligomeric or polymeric furanone magenta colorant having at least one aromatic aldehyde having a para-nitrogen and containing electron donating groups selected from the group consisting of alkyls, cycloalkyls, and polymers derived from alkyleneoxy or aryleneoxy moieties.

It is a feature of the present invention that this class of furanone magenta dyes can be easily tailored to provide particular derivatives or species within this class that possess specific physical and chemical properties.

It is another feature of the present invention that the furanone magenta dyes of the present invention may be used as either the sole colorant material in a phase change ink or can be used with other conventional phase change ink colorant materials.

It is still another feature of the present invention that these polymeric furanone magenta dyes may be employed with conventional phase change carrier components (e.g., amide waxes, resinous components, tackifiers, toughening agents, hardeners, adhesion promoters and the like).

It is yet another feature of the present invention that this class of magenta dyes can be reacted with isocyanates and anhydrides and the like to form a tailored colored resinous material or waxy material that will be more compatible with other carrier components and, thus, less likely to settle or migrate in the molten or solid state, respectively.

It is an advantage of the present invention that this class of magenta dyes is easy to manufacture.

It is another advantage of the present invention that this class of magenta dyes is easy to handle and process as part of an ink system.

These and other aspects, features and advantages are obtained by the use of an oligomeric or polymeric furanone magenta colorant derived from a 3-cyano-4-phenyl-2(5H)-furanone adduct wherein the phenyl radical possesses an oligo or polyoxyalkylene substituent.

DESCRIPTION OF THE PREFERRED EMBODIMENTS

The preferred class of furanone magenta colorants comprise compounds of formula (I):

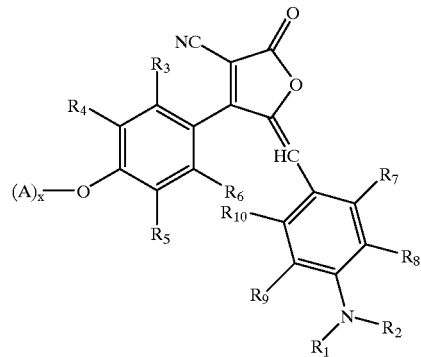

wherein A is an oxyalkylene or aryleneoxy moiety; x is an integer from 1 to about 250 or a $C_1$–$C_{60}$ linear or branched alkyl or cycloalkyl and X=1; $R_1$ and $R_2$ are individually selected from linear or branched alkyl or cycloalkyl groups having 1 to about 60 carbon atoms or are alkyleneoxy and/or aryleneoxy derivatives ranging from 2 to about 250 repeating units of a homo, random, or block co-polymer or are cycloalkyl groups including the ring N to yield ring fused tetrahydroquinolines and julolidine derivatives; $R_3$, $R_4$, $R_5$, $R_6$, $R_7$, $R_8$, $R_9$ and $R_{10}$ are individually selected from substituents selected from the group of hydrogen, alkyl groups having from 1 to about 18 carbon atoms, alkoxy groups having from 1 to about 18 carbon atoms, acetamido groups, trifluoromethyl groups, sulfonic acid groups, carboxylic acid groups, nitro groups, halogens, and carboxylic acid ester and amide derivatives.

The more preferred polyoxyalkylene and/or polyoxyarylene moieties in $A_x$ include homo, random, and block polymers arising from butylene oxide, propylene oxide, ethylene oxide, styrene oxide and mixtures thereof. More preferably, X is from about 10 to about 100 and $R_1$ and $R_2$ are either methyl or ethyl and more preferably, $R_3$ to $R_{10}$ are all hydrogen.

The chromophore shown below has the aromatic rings A and B to indicate the regiochemistry of polymeric or waxy chains attached through the heteroatoms (O,N) on rings A and B respectively:

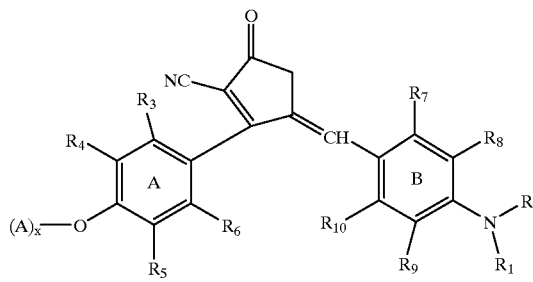

As described above, oligomeric or polymeric linkages can be effected at each site, such as oxyalkylene groups and/or oxyarylene groups, an aryl, alkyl, or aryl/alkyl (waxy) linkage; as well as resin and aryl, alkyl, or aryl/alkyl (waxy) linkages or resin and polymeric linkages. Representative oligo or polyoxyalkylene and/or polyoxyarylene groups include those derived from at least one butylene oxide, or ethylene oxide, or propylene oxide, or styrene oxide and combinations thereof. The possible resin linkages are those described hereinafter with respect to the isocyanate-derived colored resins in U.S. Pat. No. 5,780,528 issued Jul. 14, 1998 and assigned to the assignee of the present invention.

One of the most preferred compounds of the present invention is illustrated by the following formula (II):

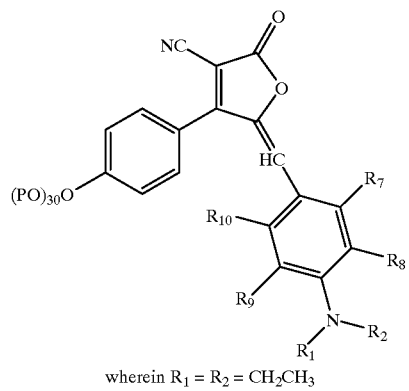

wherein $R_1 = R_2 = CH_2CH_3$

If the starting materials are a propoxylated acetophenone, bromine, ethylcyanoacetate and diethyaminobenzaldehyde, the preferred four-step synthesis of a particularly preferred species of the present colorant of the present invention is illustrated by the following reaction equations (A); (B); (C); and (D):

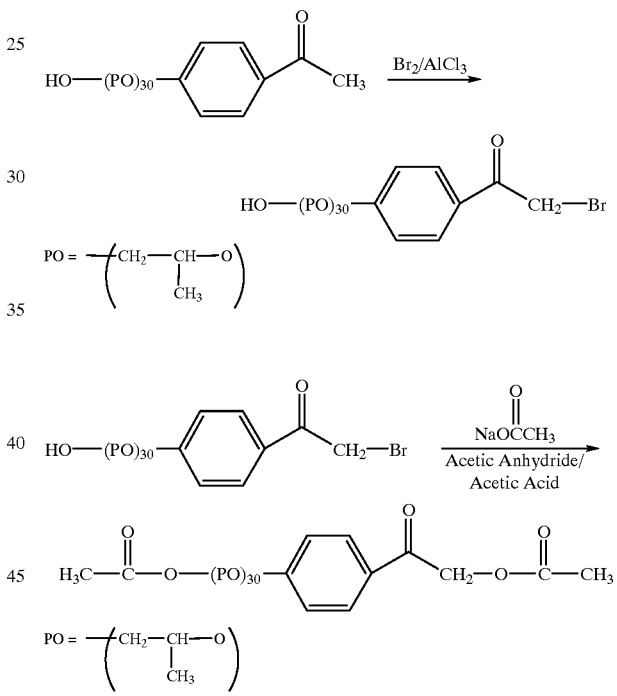

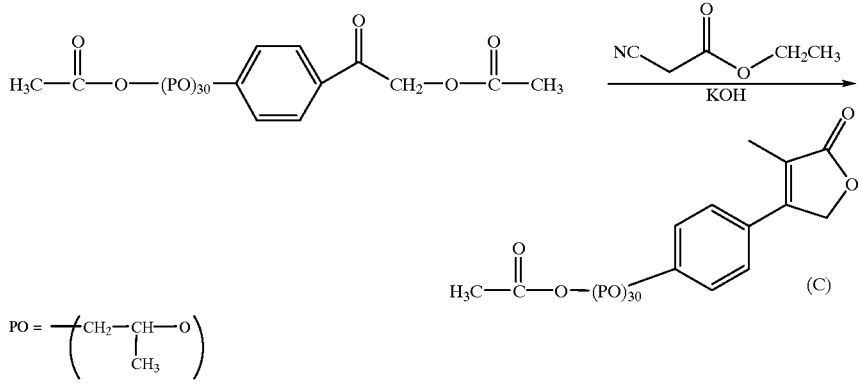

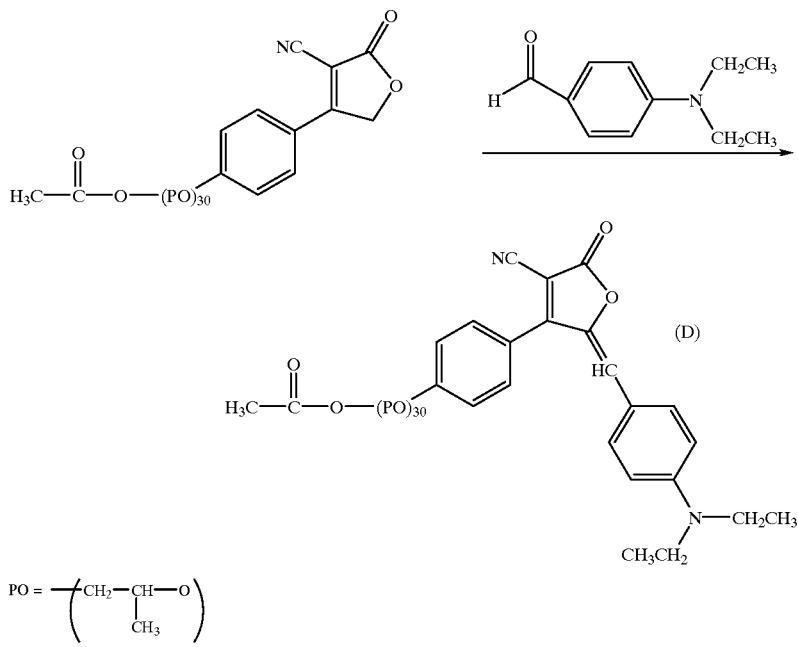

Any conventional reaction conditions normally used for similar halogenation and condensation reactions may be used in the synthesis of these compounds. For example, it may be desirable to substitute either HBr, $Cl_2$ or HCl instead of $Br_2$ as the halogenating agent in reaction equation (A).

The alkyleneoxide and/or aryleneoxide chain of these compounds of the present invention provides the polymeric functionality of these compounds and the reactive hydrogen at the end of this chain may be reactive with reagents such as anhydrides or isocyanates to make anhydride or isocyanate-derived resins or waxes.

The colorant compounds of the present invention may be combined with other conventional phase change ink colorants in making a phase change ink composition. For example, it may be desirable for certain applications to combine the present colorant or colorants with one or more polymeric dyes as described in U.S. Pat. No. 5,621,022 or conventional phase change ink colorants described in U.S. Pat. Nos. 4,889,560 and 5,372,852.

Furthermore, one or more polymeric furanone magenta colorants of the present invention (either with or without other colorants present) may be combined with conventional phase change carrier components including tetra-amide compounds, hydroxyl-functional tetra-amide compounds, mono-amides, hydroxyl-functional mono-amides, tackfiers, plasticizers, antioxidants, and viscosity reducing agents such as those disclosed in U.S. Pat. Nos. 4,889,560; 4,889,761; 5,372,852; 5,621,022; 5,700,851; 5,750,604; 5,780,528; 5,782,966; 5,783,658; 5,827,918 and 5,830,942. Suitable hardening agents may also be employed.

The preferred amounts of each colorant and carrier ingredient will depend upon the particular end-use application.

The polymeric furanone magenta colorants of the present invention may be reacted with isocyanates to make isocyanate-derived colored resins and isocyanate-derived colored waxes similar to those described in U.S. Pat. Nos. 5,750,604; 5,780,528; 5,782,966 and 5,783,658. In making these colored resins and colored waxes, the polymeric furanone magenta colorant is reacted with an isocyanate species in the same manner that the various alcohol or amine species were described as reacting with isocyanate species in these patents. Specifically, the nucleophile comprising a polymeric furanone magenta colorant can also include amines and alcohols, as disclosed in the above referenced U.S. Patents.

It is to be noted that the length of the polymer chain on the magenta chromophore can be lengthened or shortened and can consist of polymers or copolymers and oligomers selected from alkyleneoxide and/or aryleneoxides and/or those polymers consisting of branched portions prepared by the inclusion of glycidyl units. The use of glycidyl units to introduce branching on the polymeric chain enhances the number of reactive sites on the polymeric chain. This approach can be used to tailor the physical properties of the colorant and its derivatives. Typically, the useful number of repeating units on the polymer portion of the chromophore is between about 2 and about 250, more preferably between about 2 and about 100, and most preferably between about 2 and about 30.

It should also be noted that this class of magenta dyes could also be reacted with anhydrides in the type of reactions disclosed in U.S. patent application No. 09/105,308 entitled "Phase Change Ink Carrier Compositions Containing Anhydride/Alcohol-Based Adducts" filed Jun. 25, 1998, and assigned to the assignee of the present invention.

The following Examples and Comparisons are presented to illustrate the scope of the invention and to be illustrative of the formulations that can successfully be employed, without any intent to limit the invention to the specific materials, process or structure employed. All parts and percentages are by weight and all temperatures are degrees Celsius unless explicitly stated otherwise.

EXAMPLE 1

Work-up Procedures for the Propoxylated Derivatives of Acetophenone

The propoxylated derivatives described in subsequent examples exhibit a cloud point or are immiscible in water.

Hence, isolation of reaction products was accomplished by diluting the reaction mixture with an equivalent volume (or greater) of water and heating, with agitation to above the cloud point of about 60° C. to about 90° C. The mixture was then transferred to a separatory funnel and allowed to stand until phase separation occurs. The separation was easily detected visually whereby the washed and purified organic layer was isolated. The wash process can be repeated to achieve the desired level of salt or low molecular weight contaminant free propoxylated derivative. After the final wash and cloud point technique for separation, the product was dried under reduced pressure to eliminate residual amounts of water.

EXAMPLE 2

Halogenation of 4-O-poly-(oxypropylene)-4-hydroxyacetophenone

The acetophenone was halogenated by the standard procedure (Organic Syntheses, Collective Volume II, John Wiley & Sons, pp. 480—1, 1966), to produce the alpha-bromoacetophenone propoxylated derivative. Therefore, about 25.0 grams of HAPOL 30 (4-hydroxyacetophenone propoxylated with thirty equivalents of propylene oxide) available from TriQuest, LP was dissolved in approximately 30 mL of an appropriate solvent (e.g. dioxolane) and was reacted with about 2.7 grams of bromine in the presence of about 1.0 grams of anhydrous aluminum chloride catalyst according to the cited reference and heated to about 60° C. to about 80° C. The halogenated product was separated from the solvent using rotary evaporation under reduced pressure to yield a light amber colored liquid.

EXAMPLE 3

Preparation of Alpha, Omega-diacetoxy-4-O-poly-(oxypropylene)-4-hydroxyacetophenone The brominated derivative of Example 2 was diluted with about 1.3 grams acetic acid to which was added 1.8 grams acetic anhydride and about 1.1 grams sodium acetate. The reaction mixture was agitated slowly under a nitrogen atmosphere and the temperature was raised to about 70° C. to about 90° C. and maintained for about 4 hours to effect the displacement of the halogen. The acetoxy derivative was isolated by slowly pouring the reaction mixture into twice the reaction volumes of cold water, and the mixture was agitated. The reaction mixture was then heated to about 60° C. to about 80° C. and transferred to a separatory funnel and was allowed to cool to ambient temperature. The acetoxy derivative phased from the water layer, was separated, and the water wash and cloud point phasing was repeated two additional times. The phased product was dried under reduced pressure to yield a clear, dark colored oil.

EXAMPLE 4

Preparation of the Propoxylated Furanone

The acetoxy derivative of Example 3 was condensed with ethyl cyanoacetate under basic conditions followed by hydrolysis and ring closure to yield the desired furanone ring system. This reaction sequence was accomplished by adding about 1.5 grams ethyl cyanoacetate to a slowly stirred flask containing about 26.6 grams of the product from Example 3. To this reaction mixture was added slowly, about 0.53 grams sodium hydroxide while the temperature was raised to about 120° C. and agitation increased. The reaction mixture was held on temperature for about 6 hours whereupon the reaction mixture was carefully poured into about 0.5 liters of water and heated to about 60° C. to about 90° C. Purification of the light tan furanone oil was accomplished by the work-up procedure outlined in Example 1. The propoxylated furanone structure is shown below wherein R=OAc.

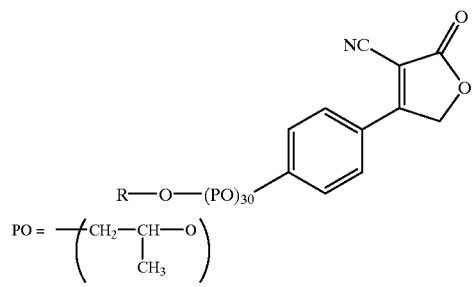

EXAMPLE 5

Preparation of a Magenta Polymeric Furanone Colorant

The propoxylated furanone of Example 4 is condensed with 4-N,N-diethyl aminobenzaldehyde under active methylene condensation conditions to yield a polymeric magenta colorant. Hence, 1 equivalent of the propoxylated furanone is mixed with 1.1 equivalents of 4-diethylaminobenzaldehyde, a catalytic amount of ammonium acetate, and about 200 mL toluene in a three necked round bottom flask equipped with a mechanical stirrer, thermometer and Dean-Stark trap/condenser apparatus. The reaction mixture is heated with agitation to the azeotropic boiling point and the reaction is continued until the stoichiometric amount of water is removed from the reaction mixture. Remaining traces of toluene are removed under reduced pressure followed by optional aqueous washings as described in Example 1. Removal of the final traces of water is accomplished under reduced pressure and gentle warming to yield a dark magenta colored liquid. The resulting product structure is shown below wherein R=OAc.

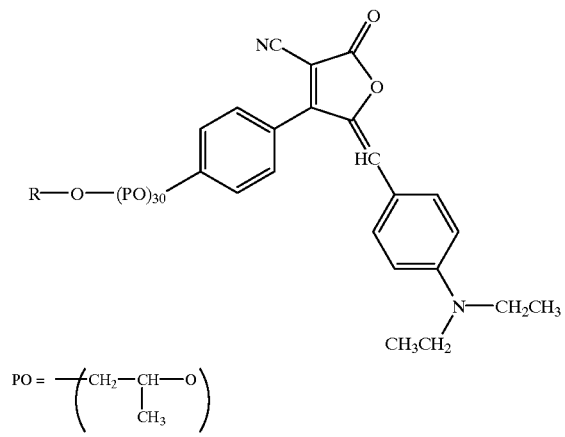

EXAMPLE 6

Polymeric Magenta Colorant based on Julolidine Aldehyde

The propoxylated furanone of Example 4 is condensed with julolidine aldehyde under active methylene condensation conditions to yield a polymeric magenta colorant. Hence 1 equivalent of the propoxylated furanone of Example 4 is mixed with 1.1 equivalents julolidine aldehyde available from Hampford Research, Inc. of Stratford, Connecticut. The condensation and work-up is conducted under identical conditions described in Example 5 to yield a dark magenta colored liquid.

EXAMPLE 7

Polymeric Magenta Colorant Based on 4-Diethylamino-o-tolualdehyde

The propoxylated furanone of Example 4 is condensed with 4-diethylamino-ortho-tolualdehyde under active methylene condensation conditions to yield a polymeric magenta colorant. Hence, 1 equivalent of the propoxylated furanone of Example 4 is mixed with 1.1 equivalents of 4-diethylamino-o-tolualdehyde available from Hampford Research, Inc. of Stratford, Conn. The condensation and work-up is conducted under identical conditions described in Example 5 to yield a dark magenta colored liquid. The structure of the resulting polymeric magenta colorant is shown below wherein R=OAc.

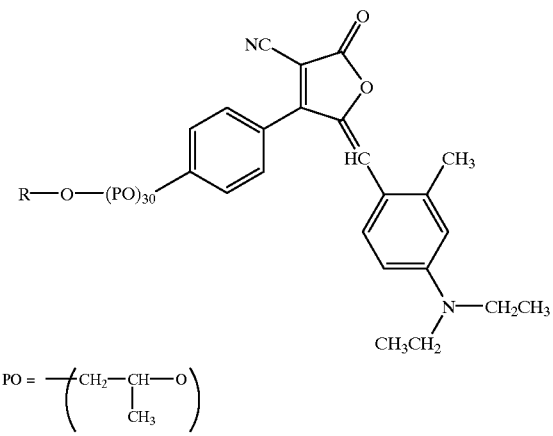

EXAMPLE 8

Omega-Acetate Hydrolysis of the Reaction Product of Example 4

Removal of the acetoxy group on the terminal hydroxyl functionality of the propyleneoxy chain of the reaction product of Example 4 is accomplished under basic conditions. Specifically, one equivalent of the diacetoxy furanone of Example 4 is treated with about 500 mL of a 40% KOH solution. The mixture is heated to about 105° C. with mechanical stirring and maintained on temperature for about 3 hours. The reaction mixture is allowed to cool to about 50° C. and is neutralized with 70% sulfuric acid. During neutralization, the reaction mixture is allowed to exotherm, but is not to exceed 90° C. The homogenous solution is transferred to a separators funnel and allowed to phase. The salt layer is removed and the product is subjected to the washing and drying procedure outlined in Example 1. The structure of the resulting compound is shown below wherein R=H.

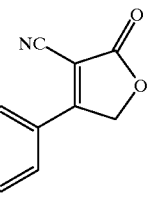
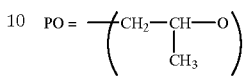

EXAMPLE 9

Preparation of a Magenta Colorant Containing a Reactive Hydroxyl

The reaction product of Example 8 is subjected to the reaction conditions of Example 5 whereby the furanone is condensed with 4-diethylamino-benzaldehyde under active methylene condensation conditions to yield a polymeric magenta colorant. Hence, 1 equivalent of the propoxylated furanone of Example 8 is mixed with 1.1 equivalents 4-diethylaminobenzaldehyde, a catalytic amount of ammonium acetate, and about 200 mL of toluene in a three necked round bottom flask equipped with a mechanical stirrer, thermometer and Dean-Stark trap/condenser apparatus. The reaction mixture is heated with agitation to the azeotropic boiling point and the reaction is continued until the stoichiometric amount of water is removed from the reaction mixture. Remaining traces of toluene are removed under reduced pressure followed by optional aqueous washings as described in Example 1. Removal of the final traces of water is accomplished under reduced pressure and gentle warming to yield a dark magenta colored liquid. The structure of the resulting colorant is shown below wherein R=H.

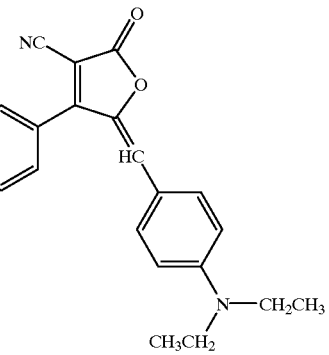
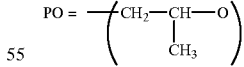

EXAMPLE 10

Preparation of a Magenta Wax

The free hydroxyl group on the polymeric furanone magenta colorant of Example 9 is available for reaction with electrophiles. Hence, one equivalent of the reaction product from Example 8 is converted to the solid, magenta wax by reaction with one equivalent of stearyl isocyanate[1]. The mixture is agitated for several minutes and about 0.5 grams of dibutyltindilaurate catalyst[2] is added and the reaction mixture heated to about 135° C. with stirring under an $N_2$ atmosphere. After about 4.0 hours at about 135° C. an FT-IR of the product is run to insure all isocyanate functionality is consumed. The absence of a peak at about 2275 cm$^{-1}$ (NCO) and the appearance (or increase in magnitude) of peaks at about 1740 to about 1680 cm$^{-1}$ and about 1540 to about 1530 cm$^{-1}$ corresponding to urethane frequencies confirm this. The final colored urethane wax product is then poured into aluminum molds and allowed to cool. The spectral strength of the dark magenta reaction product is determined using a spectrophotometric procedure based on the measurement of the colorant in solution by dissolving the solid wax in butanol and measuring the absorbance using a Perkin Elmer Lambda 2S UV/VIS spectrophotometer.

[1]Mondur O-Stearyl Isocyanate available from Bayer Corp. of Pittsburg, Pa.
[2]Dibutyltindilaurate available from Aldrich Chemicals of Milwaukee, Wis.

The structure of the resulting compound is shown below wherein R=$C_{18}H_{37}$—NHCO.

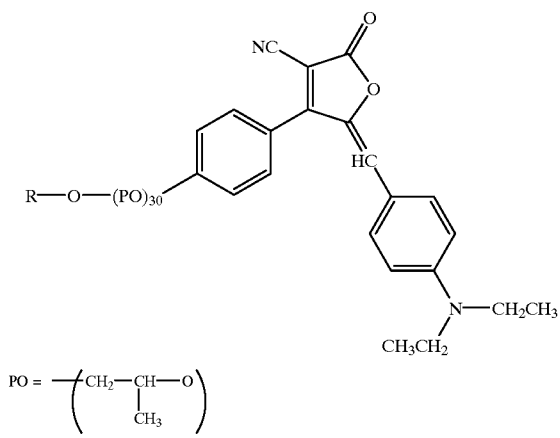

EXAMPLE 11

Preparation of a Magenta Resin

The free hydroxyl group on the polymeric furanone magenta colorant of Example 9 is available for reaction with electrophiles. Hence, one equivalent of the reaction product of Example 9, one equivalent of stearyl alcohol and one mole of isophorone diisocyanate are reacted under the conditions described in Example 5 of U.S. Pat. No. 5,780,528 issued Jul. 14, 1998 and assigned to the assignee of the present invention. The mixed darkly magenta colored urethane reaction product is poured hot into aluminum pans and allowed to harden.

EXAMPLE 12

Preparation of Phase Change Ink Base

A generic phase change ink base is prepared by melting together in weight proportions about 49% stearyl stearamide (Kemamide S-180 available from Witco Chemical Company of Memphis Tenn.), about 49% of a mixed urethane resin (described in Example 4 of U.S. Pat. No. 5,782,966 issued July 21, 1998 and assigned to the assignee of the present invention) and 2% Naugard 445 anti-oxidant (available from Uniroyal Chemical Company of Oxford, Conn.) according to the general procedures described above.

EXAMPLE 13

Preparation of a Magenta Inks

| Magenta from Example # | % Magenta | Phase Change Ink Base % of |
|---|---|---|
| A. | 6 | 8 | 92 |
| B. | 9 | 5 | 95 |
| C. | 10 | 15 | 85 |
| D. | 11 | 25 | 75 |

Inks are formulated according to the above table of approximate percentages and to the general directions supplied in the following section for ink formulation and evaluation. All inks are adjusted to identical spectral strengths and to identical viscosities suitable for providing a useful, colored mark when printed. The inks are printed for evaluation using a Tektronix Phaser® color printer. In each case, the inks demonstrate suitability for use in a Tektronix piezo driven print head and provide good physical and mechanical properties on printed substrates.

Standard Procedures and Processes Related to the Production of Inks

1. Ink Constituents

The ink formulations are composed of ingredients typically found in Tektronix phase change inks with the exception of the materials described within the current invention. The formulation techniques and ancillary materials have been disclosed in the previously referenced Tektronix patents. The formulation materials include but are not limited to: viscosity modifiers, colorants, dyes, pigments, antioxidants, toughening agents, waxes (ester, amide, natural and synthetic), plasticizers, organoleptic constituents, color developers, resins (urethane, urea and urethane/urea), polymeric colorants, and resins derived from polymeric colorants.

2. Ink Formulation

Inks are prepared by melting the desired ingredients in a stainless steel beaker and blending with mechanical agitation. Typical blending temperatures range from about 80° C. to about 140° C. Blending is accomplished using a temperature controlled mantle and agitation for about one hour. An aliquot of ink is removed and characterized, typically by a select few physical properties which include: spectral strength, viscosity, glass transition temperature and melting point. These properties are adjusted by reformulation of the ink as required to work in a Tektronix Phaser® color printer or other printing or marking device.

3. Ink Processing

The final inks are filtered through a heated Mott apparatus (available from Mott Metallurgical) using #3 Whatman filter paper and a pressure of about 15 psi. The filtered phase change ink is poured into molds and allowed to solidify to form ink sticks.

4. Ink Analysis and Characterization

The final ink products are characterized by the following physical properties: viscosity of about 13 cPs as measured by a Ferranti-Shirley cone-plate viscometer at about 140° C. and adjusted with stearyl stearamide to lower the viscosity, a melting point (expected range about 85° C. to about 160° C.) as measured by differential scanning calorimetry using a DuPont 2100 calorimeter, and a glass transition temperature (expected range from about −25° C. to about 100° C.) as measured by Dynamic Mechanical Analysis using a Rheometrics Solids Analyzer (RSAII). The spectral strength of the ink is determined using a spectrophotometric procedure based on the measurement of the colorant in solution by dissolving the solid ink in butanol and measuring the absorbance using a Perkin Elmer Lambda 2S UV/V is spectrophotometer. Spectral intensity is adjusted as required to meet the printing application.

5. Ink Performance Testing in the Print Head and the Transfixing Process

The inks are evaluated in Tektronix Phaser® color printers for reliable jetting characteristics in a Tektronix piezoelectrically driven print head. Measures include drop mass and response to jetting frequency, applied voltage and waveforms employed for ejection. Desired observations include an ink which jets and is capable of producing ink droplets at a useful marking rate. Furthermore, the print head operation is not impeded after several freeze-thaw cycles of print head operation. That is, no orifice clogging or diminished jetting characteristics are observed.

The inks are evaluated for their film splitting characteristics in the offset printing process employed by Tektronix Phaser® color printers as represented by a Phaser 340 printer. A description of these requirements is found in "Rheological, Thermo-Mechanical and Viscoelastic Requirements of a Phase Change Ink for an Offset Ink Jet Printing Process," L. Bui, et al., Proceedings of the IS&T's Eleventh International Congress on Advances in Non-Impact Printing Technologies, 1995. The inks are ejected onto the rotating drum containing a sacrificial silicone oil intermediate transfer liquid layer. The image is then transferred to the desired substrate by the transfixing process. The inks are expected to exhibit greater than 90% transfer from the drum to the substrate as measured by a chase sheet through the print process as a follower after the printed image is prepared. The inks are also evaluated for the absence of cohesive failure between ink layers built up on the rotating drum prior to transfixing. The print process parameters of substrate pre-heating, drum temperature, and transfixing pressure are adjusted to optimize the image and print quality of the final printed article.

6. Print and Performance Testing

The inks are tested in a Tektronix Phases® 340 printer, which uses an offset transfer printing system. The inks are found to completely transfer and to give images of good color, print quality and durability either as primary colors or when used in combination with each other or with the commercially available Phaser 340 printer inks.

The inks are poured into molded HIPSMA (High Impact Polystyrene/Maleic Anhydride) plastic cups or tubs and allowed to cool and solidify. The finished solid ink sticks from these examples have excellent surface finishes and good release properties from the plastic cups.

A blocking test can be used to evaluate the inks following the procedure described on page 56 of the Proceedings of NIP12: The Twelfth International Congress on Digital Printing Technologies, published in 1996 by the Society for Imaging Science and Technology.

Prints made from the preceding example are expected to provide durability features commensurate with laser printer hardcopy or prints prepared by aqueous ink jet devices, or commercial offset printing techniques. Quantitative comparisons using a Taber Abrasion method (ASTM D4060) provides an indication of the durability provided by the polymeric characteristics of the subject colorant and inks prepared from them also show improved resistance to cracking when the printed article is folded.

While the invention has been described above with reference to specific embodiments thereof, it is apparent that many changes, modifications, and variations can be made without departing from the inventive concept disclosed herein. For example, in the preceding discussion and Examples a polymer on one, but not both aromatic rings of the chromophore has been employed. It is to be understood that polymer chains can be employed on either or both aromatic rings. Where employed on both aromatic rings, the polymer chains are likely coupled through the heteroatoms (nitrogen, oxygen) of each ring. Polymer length and selection can vary according to the physical properties desired. Subsequent reaction of hydroxy functionality on the polymer chain with electrophiles to produce resins or waxes is also possible. When the colorant of the present invention is used in a reaction sequence to prepare a resin from a diisocyanate, the molar ratios of colorant and the other nucleophile or nucleophiles can be altered to yield materials having a range of physical and mechanical properties.

A polymeric chain can also be introduced into the non-polymeric dyestuffs disclosed in U.S. Pat. Nos. 3,661,899 and 3,468,912 by using similar methodology disclosed herein.

Lastly, the colorants disclosed herein can have utility in other printing processes besides ink jet, such as gravure, flexographic, intaglio, and letterpress.

Accordingly, the spirit and broad scope of the appended claims is intended to embrace all such changes, modifications and variations that may occur to one of skill upon a reading of the disclosure. All patent applications, patents and other publications cited herein are incorporated by reference in their entirety.

What is claimed is:

1. A furanone magenta colorant comprising a furanone magenta chromophore having a furanone adduct, the adduct containing at least one oligo- or polyalkoxylated or -aryloxylated phenyl radical, the chromophore further being derived from at least one aromatic aldehyde having a para-nitrogen and containing electron donating groups selected from the group consisting of alkyls, cycloalkyls, and oligomers or polymers derived from alkyleneoxy or aryleneoxy moieties.

2. The colorant according to claim 1 wherein the at least one aromatic aldehyde from which the chromophore is derived includes at least one dialkylaminobenzaldehyde functional group.

3. The colorant according to claim 1 wherein the chromophore comprises a 3-cyano-4-(p-polyoxyalkylenephenyl)-2(5H)-furanone moiety.

4. The colorant according to claim 1 wherein the magenta colorant is a compound of the formula:

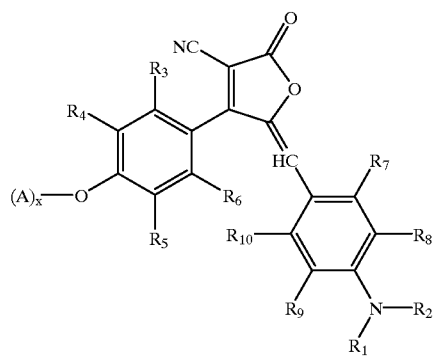

wherein A is an alkyleneoxy and/or aryleneoxy moiety, and x is an Integer from 2 to about 250; $R_1$ and $R_2$ are Individually selected from linear or branched alkyl or cycloalkyl groups having 1 to about 60 carbon atoms or are alkyleneoxy or aryleneoxy derivatives ranging from 2 to about 250 repeating units of a homo or block co-polymer or are cycloalkyl groups including the ring N to yield ring fused tetrahydroquinolines and julolidine derivatives; and $R_3$, $R_4$, $R_5$, $R_6$, $R_7$, $R_8$, $R_9$ and $R_{10}$ are individually selected from substituents selected from the group consisting of hydrogen, alkyl groups having from 1 to about 18 carbon atoms, alkoxy groups having from 1 to about 18 carbon atoms, acetamido groups, trifluoromethyl groups, sulfonic acid groups, carboxylic acid groups, nitro groups, halogens and carboxylic acid ester and amide derivatives.

5. The colorant according to the structure in claim 4 wherein $A_x$ includes polyoxyalkylene and/or polyoxyarylene moieties.

6. The colorant according to the structure in claim 5 wherein the polyoxyalkylene and/or polyoxyarylene moieties further include homo, random, and block polymers derived from at least one member selected from the group consisting of butylene oxide, propylene oxide, ethylene oxide, and styrene oxide and combinations thereof.

7. The colorant according to claim 1 wherein the colorant is used in a phase change ink.

8. The phase change ink according to claim 7 wherein the ink includes one or more components selected from the group consisting of a tetra-amide, a hydroxyl-functional tetra-amide compound, a mono-amide, a hydroxyl-functional mono-amide, a plasticizer, a tackifier, an isocyanate-derived wax and an isocyanate-derived resin.

9. The colorant according to claim 1 wherein the colorant is reacted with an anhydride or an isocyanate to form a compound that is a colored resin or a colored wax.

10. A process for making a furanone magenta colorant comprising the steps of:

(1) subjecting an oligo- or polyalkoxylated or -aryloxylated acetophenone to a halogenation reaction to form a halogenated oligo- or polyalkoxylated or -aryloxylated acetophenone;

(2) subjecting the halogenated oligo- or polyalkoxylated or -aryloxylated acetophenone to an organocarboxylate substitution reaction to form an organocarboxylate diester of the oligo- or polyalkoxylated or -aryloxylated acetophenone;

(3) condensing the organocarboxylate diester of the oligo- or polyalkoxylated or -aryloxylated acetophenone with an alkylcyanoacetate in the presence of a base to form an oligo- or polyalkoxylated or -aryloxylated furanone derivative: and (4) condensing the oligo- or polyalkoxylated or -aryloxylated furanone derivative with an electron rich aromatic aldehyde to form a furanone magenta colorant having at least one oligo- or polyalkoxylated or -aryloxylated phenyl radical and being derived from at least one aromatic aldehyde having a para-nitrogen and containing electron donating groups selected from the group consisting of alkyls, cycloalkyls, and oligomers or polymers derived from alkyleneoxy or aryleneoxy moieties.

11. A phase change ink composition comprising the combination of a phase change ink carrier and a furanone magenta colorant having a furanone adduct, the adduct containing at least one oligo- or polyalkoxylated or -aryloxylated phenyl radical and being derived from at least one aromatic aldehyde having a para-nitrogen and containing electron donating groups selected from the group consisting of alkyls, cycloalkyls, and oligomers or polymers derived from alkyleneoxy or aryleneoxy moieties.

12. The phase change ink composition according to claim 11 wherein the at least one aromatic aldehyde from which the chromophore is derived includes at least one dialkylaminobenzaldehyde functional group.

13. The phase change ink composition according to claim 11 wherein the chromophore comprises a 3-cyano-4-(p-polyoxyalkylenephenyl)-2(5H)-furanone moiety.

14. The phase change ink composition according to claim 11 wherein the magenta colorant is a compound of the formula:

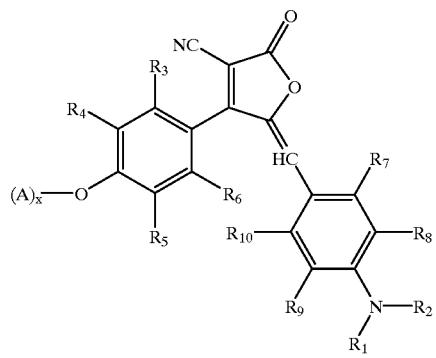

wherein A is an alkyleneoxy and/or aryleneoxy moiety, x Is an integer from 2 to about 250, $R_1$ and $R_2$ are individually selected from linear or branched alkyl or cycloalkyl groups having 1 to about 60 carbon atoms or are alkyleneoxy or aryleneoxy derivatives ranging from 2 to about 250 repeating units of a homo or block co-polymer or are cycloalkyl groups including the ring N to yield ring fused tetrahydroquinolines and Julolidine derivatives; and $R_3$, $R_4$, $R_5$, $R_6$, $R_7$, $R_8$, $R_9$ and $R_{10}$ are individually selected from substituents selected from the group consisting of hydrogen, alkyl groups having from 1 to about 18 carbon atoms, alkoxy groups having from 1 to about 18 carbon atoms, acetamido groups, trifluoromethyl groups. sulfonic acid groups, carboxylic acid groups, nitro groups, halogens and carboxylic acid ester and amide derivatives.

15. The phase change ink composition according to the structure in claim 14 wherein A. includes polyoxyalkylene and/or polyoxyarylene moieties.

16. The phase change ink composition according to the structure in claim 15 wherein the polyoxyalkylene and/or polyoxyarylene moieties further include homo, random, and block polymers derived from at least one member selected from the group consisting of butyrene oxide, propylene oxide, ethylene oxide, and styrene oxide and combinations thereof.

* * * * *